(12) United States Patent
Sokolov et al.

(10) Patent No.: US 8,562,638 B2
(45) Date of Patent: Oct. 22, 2013

(54) EMBOLUS BLOOD CLOT FILTER WITH FLOATING FILTER BASKET

(75) Inventors: Eugene Lvovitch Sokolov, Gatchina (RU); Andrzej J. Chanduszko, Chandler, AZ (US)

(73) Assignee: C.R. Bard, Inc., Murray Hill, NJ (US)

( * ) Notice: Subject to any disclaimer, the term of this patent is extended or adjusted under 35 U.S.C. 154(b) by 1187 days.

(21) Appl. No.: 12/096,814

(22) PCT Filed: Dec. 29, 2006
(Under 37 CFR 1.47)

(86) PCT No.: PCT/US2006/062720
§ 371 (c)(1),
(2), (4) Date: Apr. 3, 2009

(87) PCT Pub. No.: WO2007/079408
PCT Pub. Date: Jul. 12, 2007

(65) Prior Publication Data
US 2010/0063533 A1    Mar. 11, 2010

Related U.S. Application Data

(60) Provisional application No. 60/754,599, filed on Dec. 30, 2005.

(51) Int. Cl.
*A61M 29/00* (2006.01)
(52) U.S. Cl.
USPC ........................................................ 606/200
(58) Field of Classification Search
USPC ........................................................ 606/200
See application file for complete search history.

(56) References Cited

U.S. PATENT DOCUMENTS

| | | | |
|---|---|---|---|
| 4,425,908 A | * | 1/1984 | Simon ........................ 128/899 |
| 4,494,531 A | | 1/1985 | Gianturco |
| 4,619,246 A | * | 10/1986 | Molgaard-Nielsen et al. ........................ 128/899 |

(Continued)

FOREIGN PATENT DOCUMENTS

| EP | 188927 B1 | 7/1989 |
|---|---|---|
| WO | WO 2006/124405 A2 | 11/2006 |
| WO | WO 2007/021340 A1 | 2/2007 |

OTHER PUBLICATIONS

International Search Report, PCT/US2006/062720.

(Continued)

*Primary Examiner* — Gary Jackson
*Assistant Examiner* — Jonathan Hollm
(74) *Attorney, Agent, or Firm* — Garvey, Smith, Nehrbass & North, L.L.C.; Seth M. Nehrbass; Charles C. Garvey, Jr.

(57) ABSTRACT

A blood filter device for placement in a blood vessel including a plurality of anchor members disposed radially and extending angularly about a first hub. A filter basket is preferably positioned upstream from the anchor members. The anchor members each include a hook configured to penetrate the vessel wall to prevent longitudinal movement due to blood flow. The filter basket is made up of a number of filter members configured to retain blood clots within the basket without completely blocking blood flow or applying additional force to vessel walls. Portions of the filter members may project radially outward to position the basket near the vessel centerline, but the filter basket preferably does not include hooks or anchors for anchoring the filter basket to the blood vessel.

19 Claims, 17 Drawing Sheets

(56) References Cited

U.S. PATENT DOCUMENTS

| | | | |
|---|---|---|---|
| 4,688,553 A | 8/1987 | Metals | |
| 5,108,418 A | 4/1992 | Lefebvre | |
| 5,375,612 A * | 12/1994 | Cottenceau et al. | 128/899 |
| 5,634,942 A * | 6/1997 | Chevillon et al. | 623/1.1 |
| 5,669,933 A | 9/1997 | Simon et al. | |
| 5,709,704 A | 1/1998 | Nott et al. | |
| 5,720,764 A * | 2/1998 | Naderlinger | 606/200 |
| 5,776,162 A | 7/1998 | Kleshinski | |
| 5,800,457 A * | 9/1998 | Gelbfish | 606/200 |
| 5,836,968 A * | 11/1998 | Simon et al. | 606/200 |
| 6,007,558 A | 12/1999 | Ravenscroft et al. | |
| 6,080,178 A | 6/2000 | Meglin | |
| 6,156,055 A | 12/2000 | Ravenscroft | |
| 6,176,871 B1 | 1/2001 | Pathak et al. | |
| 6,193,739 B1 | 2/2001 | Chevillon et al. | |
| 6,258,026 B1 | 7/2001 | Ravenscroft et al. | |
| 6,267,776 B1 | 7/2001 | O'Connell | |
| 6,273,900 B1 | 8/2001 | Nott et al. | |
| 6,331,183 B1 | 12/2001 | Suon | |
| 6,371,971 B1 * | 4/2002 | Tsugita et al. | 606/200 |
| 6,436,120 B1 | 8/2002 | Meglin | |
| 6,443,972 B1 * | 9/2002 | Bosma et al. | 606/200 |
| 6,468,290 B1 | 10/2002 | Weldon et al. | |
| 6,468,291 B2 * | 10/2002 | Bates et al. | 606/200 |
| 6,506,205 B2 * | 1/2003 | Goldberg et al. | 606/200 |
| 6,517,559 B1 * | 2/2003 | O'Connell | 606/158 |
| 6,540,767 B1 | 4/2003 | Walak et al. | |
| 6,589,266 B2 * | 7/2003 | Whitcher et al. | 606/200 |
| 6,623,506 B2 * | 9/2003 | McGuckin et al. | 606/200 |
| 6,746,469 B2 * | 6/2004 | Mouw | 606/200 |
| 6,783,538 B2 * | 8/2004 | McGuckin et al. | 606/200 |
| 6,872,217 B2 * | 3/2005 | Walak et al. | 606/200 |
| 7,056,286 B2 | 6/2006 | Ravenscroft et al. | |
| 7,347,869 B2 * | 3/2008 | Hojeibane et al. | 623/1.24 |
| 7,578,830 B2 * | 8/2009 | Kusleika et al. | 606/194 |
| 7,780,696 B2 * | 8/2010 | Daniel et al. | 606/200 |
| 7,803,171 B1 * | 9/2010 | Uflacker | 606/200 |
| 7,842,064 B2 * | 11/2010 | Huter et al. | 606/200 |
| 7,909,847 B2 * | 3/2011 | McGuckin et al. | 606/200 |
| 7,947,060 B2 * | 5/2011 | Mazzocchi et al. | 606/200 |
| 2001/0003796 A1 | 6/2001 | Yang et al. | |
| 2001/0039432 A1 | 11/2001 | Whitcher et al. | |
| 2003/0071285 A1 * | 4/2003 | Tsukernik | 257/200 |
| 2003/0074019 A1 * | 4/2003 | Gray et al. | 606/200 |
| 2003/0187495 A1 | 10/2003 | Cully et al. | |
| 2003/0208227 A1 * | 11/2003 | Thomas | 606/200 |
| 2004/0073252 A1 * | 4/2004 | Goldberg et al. | 606/200 |
| 2004/0186512 A1 | 9/2004 | Bruckheimer et al. | |
| 2004/0193209 A1 | 9/2004 | Pavcnik et al. | |
| 2005/0055045 A1 | 3/2005 | DeVries et al. | |
| 2005/0085847 A1 | 4/2005 | Galdonik et al. | |
| 2005/0159771 A1 * | 7/2005 | Petersen | 606/200 |
| 2005/0159773 A1 | 7/2005 | Broome et al. | |
| 2005/0163821 A1 | 7/2005 | Sung et al. | |
| 2005/0165441 A1 * | 7/2005 | McGuckin et al. | 606/200 |
| 2005/0177224 A1 * | 8/2005 | Fogarty et al. | 623/1.35 |
| 2005/0234503 A1 | 10/2005 | Ravenscroft et al. | |
| 2005/0277977 A1 | 12/2005 | Thornton | |
| 2006/0036279 A1 | 2/2006 | Eidenschink et al. | |
| 2006/0095068 A1 | 5/2006 | WasDyke et al. | |
| 2007/0088381 A1 * | 4/2007 | McGuckin et al. | 606/200 |
| 2009/0105747 A1 * | 4/2009 | Chanduszko et al. | 606/200 |
| 2009/0182370 A1 * | 7/2009 | Volobuyev et al. | 606/200 |
| 2009/0306703 A1 * | 12/2009 | Kashkarov et al. | 606/200 |
| 2010/0318115 A1 * | 12/2010 | Chanduszko et al. | 606/200 |

OTHER PUBLICATIONS

International Preliminary Report on Patentability and Written Opinion of the International Searching Authority in PCT/US06/62720.

* cited by examiner

EMBOLUS BLOOD CLOT FILTER WITH FLOATING FILTER BASKET

This is a National Stage application under 35 U.S.C. 371 of International Application No. PCT/US2006/062720, filed Dec. 29, 2006, which claims the benefit of priority to U.S. Provisional Patent Application No. 60/754,599, filed Dec. 30, 2005 each of which is incorporated by reference in its entirety. This invention is related to the subject matter shown and described in the following: (i) PCT International Application No. PCT/US06/62722, filed Dec. 29, 2006, entitled "Removable Blood Clot Filter with Edge For Cutting Through the Endothelium" and claiming the benefit of priority to U.S. Provisional Patent Application No. 60/754,600, filed Dec. 30, 2005; (ii) PCT International Application No. PCT/US06/62719, filed Dec. 29, 2006, entitled "Embolus Blood Clot Filter with Post Delivery Actuation," and claiming the benefit of priority to U.S. Provisional Patent Application No. 60/754,633, filed Dec. 30, 2005; (iii) PCT International Application No. PCT/US06/62725, filed Dec. 29, 2006, entitled "Embolus Blood Clot Filter Delivery System," and claiming the benefit of priority to U.S. Provisional Patent Application No. 60/754,636, filed Dec. 30, 2005; (iv) PCT International Application No. PCT/US06/62733, filed Dec. 29, 2006, entitled "Embolus Blood Clot Filter Removal System and Method," and claiming the benefit of priority to U.S. Provisional Patent Application No. 60/754,598, filed Dec. 30, 2005; and (v) PCT International Application No. PCT/US06/62730, filed Dec. 29, 2006, entitled "Embolus Blood Clot Filter with Bio-Resorbable Coated Filter Members," and claiming the benefit of priority to U.S. Provisional Patent Application No. 60/754,597, entitled "Embolus Blood Clot Filter with Retainers on Locator Filter Members," filed Dec. 30, 2005, each of which is hereby incorporated by reference in its entirety.

TECHNICAL FIELD

This invention relates to a filter device that can be placed in a blood vessel to reduce the risk of embolisms and, more particularly to a filter that will not increase pressure applied to the blood vessel walls as emboli are captured from the blood.

BACKGROUND ART

In recent years, a number of medical devices have been designed which are adapted for compression into a small size to facilitate introduction into a vascular passageway and which are subsequently expandable into contact with the walls of the passageway. These devices, among others, include blood clot filters which expand and are held in position by engagement with the inner wall of a vein, such as the vena cava. Such filters include structure to anchor the filter in place within the vena cava, such as elongate diverging anchor members with hooked ends that penetrate the vessel wall and positively prevent longitudinal migration of the filter within the vessel.

A number of conditions and medical procedures subject the patient to a short term risk of pulmonary embolism which can be alleviated by a filter implant. In such cases, the filter catches and retains emboli to prevent them from reaching the lungs or the brain. A number of configurations of blood filters are known. An example of such a filter is disclosed in U.S. Pat. No. 6,258,026 and illustrated in FIGS. 16 and 17.

Typical previously known blood filters include a number of locator members 20 and anchor members 30. The locator members 20 and anchor members 30 may be offset one from the other about the longitudinal axis of the filter 1, as shown in FIG. 17. Hooks 40 positioned on the distal ends of the anchor members 30 engage the blood vessel wall to prevent longitudinal movement within a blood vessel. When in place in a blood vessel 6, anchor members 30 form a first filtering zone 10 and locator members 20 form a second filter zone 11, as shown in FIG. 18.

First filtering zone 10, which is defined by anchor members 30, receives blood flow 8 before blood reaches the remainder of the filter 1. So emboli 5 tend to be captured preferentially in first filtering zone 10, as illustrated in FIG. 18. This result has disadvantages when a significant mass of emboli 5 are retained. For one, under the pressure of blood flow 8, the emboli 5 will press with a force $F_0$ against anchor member 30 which results in a radial force component $F_2$. Acting as a lever, anchor member 30 translates the radial force component $F_2$ into greater stress 100 applied to the blood vessel walls 6 by the hooks 40. Over time, the stress 100 applied to the vessel walls 6 may lead to vascular injury or disease. In addition, since the anchor members 30 must engage the vessel wall to hold the filter 1 in place, the first filtering zone 10 is susceptible to complete filling such that emboli 5 span the entire cross section of the blood vessel, as illustrated in FIG. 19. If this happens, in addition to increasing the stress 100 applied to the blood vessel wall 6, the captured emboli will completely block blood flow through the vessel.

Accordingly, there is a need for a blood filter which will not increase stress applied to blood vessel walls as emboli are captured and will not completely block blood flow if filled with emboli.

DISCLOSURE OF INVENTION

A preferred device provides for filtration of emboli in a blood vessel without the captured emboli causing increased stress on the blood vessel walls or total blockage of blood flow.

In an embodiment, a blood filter includes first and second hubs, at least one anchor, and a filter basket preferably configured not to anchor to the blood vessel wall. The first and second hubs may be disposed along a longitudinal axis. Anchor members extend from the first hub and engage the blood vessel wall with hooks to prevent longitudinal movement of the filter. The second hub is coupled to the first hub, such as by means of a connector (e.g., wire or bundle of wires). The filter basket is made up of a number of filter members that are coupled to the second hub and project radially and longitudinally away from the second hub. A retainer member limits radial expansion of the filter members. In an embodiment, the retainer member is configured to project radially so as to position the open end of the filter basket within the blood vessel. In an embodiment, the filter basket further includes two or more retainer members separated by a distance along the longitudinal axis to further limit radial expansion of the filter members. Preferably, the filter members and retainer members are made from a shape memory alloy, such as Nitinol.

In another embodiment, a blood filter includes first and second hubs, at least one anchor, and a filter basket preferably configured not to anchor to the blood vessel wall. The first and second hubs may be disposed along a longitudinal axis. Anchor members extend from the first hub and engage the blood vessel wall with hooks to prevent longitudinal movement of the filter. The second hub is coupled to the first hub, such as by means of a wire or bundle of wires. The filter basket is made up of a number of filter members that are coupled to the second hub and project radially and longitudinally away from the second hub. A retainer member limits radial expansion of the filter members. The filter members may be configured to project radially at their distal ends so as to position the open end of the filter basket within the blood vessel. In an embodiment, the filter basket further includes two or more retainer members separated by a distance along the longitudinal axis to further limit radial expansion of the filter members.

In another embodiment, a blood filter includes first and second hubs, at least one anchor, and a filter basket preferably configured not to anchor to the blood vessel wall. The first and second hubs may be disposed along a longitudinal axis. Anchor members extend from the first hub and engage the blood vessel wall with hooks to prevent longitudinal movement of the filter. The second hub is coupled to the first hub, such as by means of a wire or bundle of wires. The filter basket is made up of at least one filter member that is coupled to the second hub and shaped in the form of a helix. If more than one helical filter member is included, the helical filter members are angularly offset about the longitudinal axis. The filter members may include a distal portion which projects radially outward so as to position the open end of the filter basket within the blood vessel.

In another embodiment, a blood filter includes a single hub, a plurality of anchor members, and a filter basket preferably configured not to anchor to the blood vessel wall. The hub may be disposed along a longitudinal axis. Anchor members extend from the hub and engage the blood vessel wall with hooks to prevent longitudinal movement of the filter. The filter basket is made up of a plurality of filter members each of which has a generally linear extended segment and a filter basket segment. The extended segments of the filter members are coupled to the hub. The filter basket segments may form a rectilinear filter basket, a birdcage-like filter basket or a helical filter basket. A retainer member may be coupled to the filter basket segments, and the filter members may farther include a distal segment which projects radially outward so as to position the open end of the filter basked within the blood vessel.

In another embodiment, a blood filter includes first, second and third hubs, at least one anchor, and first and second filter baskets that are preferably configured not to anchor to the blood vessel wall. The first, second and third hubs may be disposed along a longitudinal axis. Anchor members extend from the first hub and engage the blood vessel wall with hooks to prevent longitudinal movement of the filter. The second hub is coupled to the first hub, such as by means of a connector (e.g., wire or bundle of wires). The first filter basket is made up of a number of filter members that are coupled to the second hub and project radially and longitudinally away from the second hub. A retainer member limits radial expansion of the first filter members. In an embodiment, the retainer member is configured to project radially so as to position the open end of the first filter basket within the blood vessel. The third hub is coupled to the second hub, such as by means of a connector (e.g., wire or bundle of wires). The second filter basket is made up of a number of second filter members that are coupled to the third hub and project radially and longitudinally away 10 from the third hub. A second retainer member limits radial expansion of the second filter members. In an embodiment, the second retainer member is configured to project radially so as to position the open end of the second filter basket within the blood vessel. Preferably, the filter members and retainer members are made from a shape memory alloy, such as Nitinol.

The various embodiments provide a filter that includes a filtering basket that is positioned upstream (with respect to blood flow through the vessel) from the filter's anchor members. The embodiments provide a filter that can remove emboli from the blood before they encounter the filter's anchoring members. So positioned, the filter basket can be smaller in cross section than the blood vessel so a full filter does not clog the blood vessel. Also, the volume of the filter basket can be controlled by lengthening the filter members so a larger volume of emboli can be removed without leading to blockage of the blood vessel.

BRIEF DESCRIPTION OF THE DRAWINGS

The accompanying drawings, which are incorporated herein and constitute part of this specification, illustrate example embodiments of the invention, and, together with the general description given above and the detailed description given below, explain features of the invention.

MODE(S) FOR CARRYING OUT THE INVENTION

The various embodiments will be described in detail with reference to the accompanying drawings. Wherever possible, the same reference numbers will be used throughout the drawings to refer to the same or like parts.

As used herein, the terms "about" or "approximately" for any numerical values or ranges indicate a suitable dimensional tolerance that allows the part or collection of components to function for its intended purpose as described herein. Also, as used herein, the terms "patient", "host" and "subject" refer to any human or animal subject and are not intended to limit the systems or methods to human use, although use of the subject invention in a human patient represents a preferred embodiment.

FIGS. 1-15A illustrate various embodiments of blood filters which filter emboli in a blood vessel of a subject such that the captured emboli tend not to cause increased pressure on the blood vessel walls or total blockage of blood flow. The preferred embodiments of the blood filter provide a first filtering element or filter basket, upstream with respect to the filter's anchor members. When appropriately located and oriented within a blood vessel, the filter basket is able to remove emboli from the blood before the emboli encounter the anchor members. The filter basket can be configured to have a smaller open face (i.e., smaller cross section) than the blood vessel's cross section. Preferably, the filters define a filtering volume that can be adjusted to retain more emboli without changing the filter's anchor members.

Figure 1:
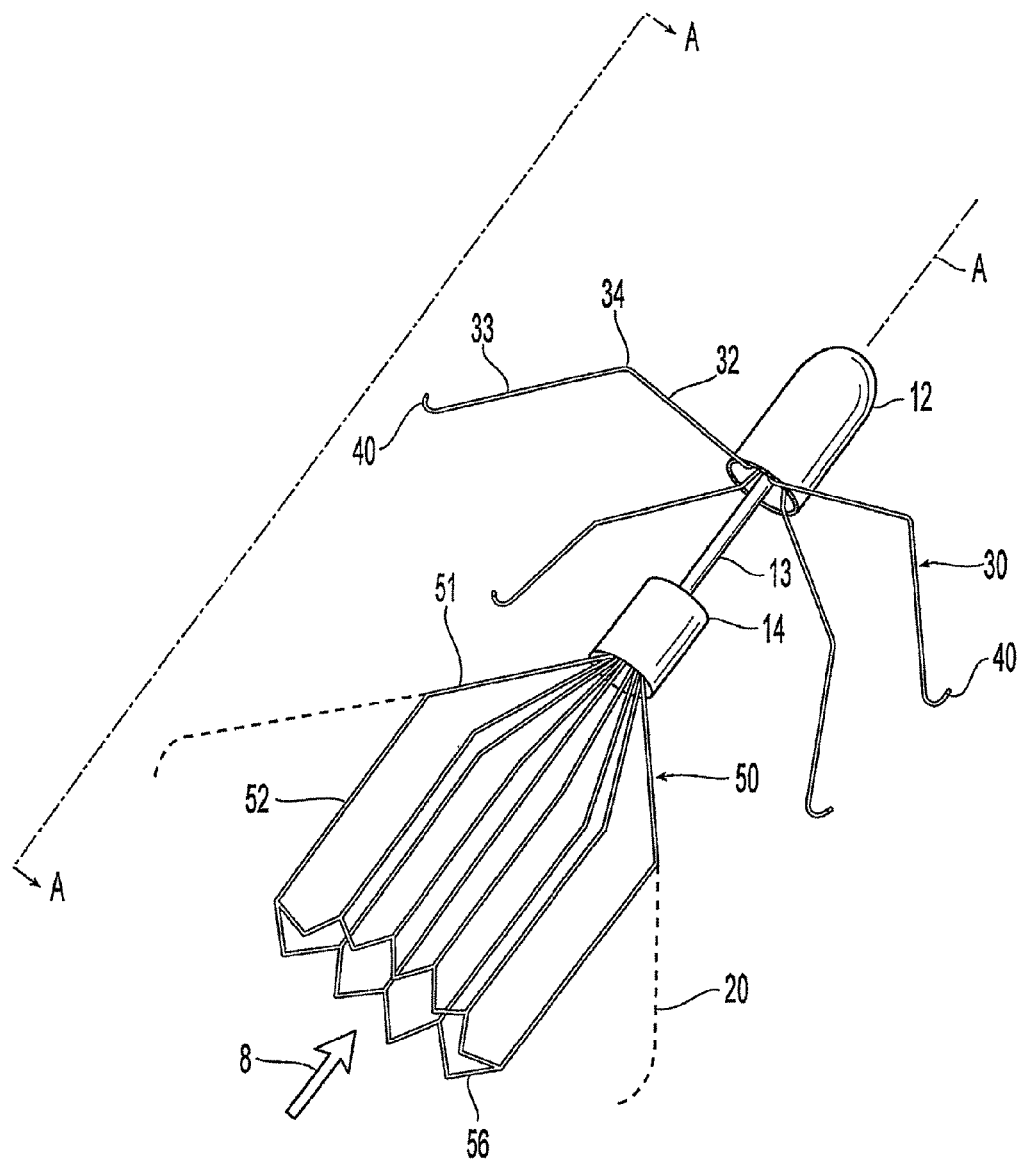
FIG. 1 is a perspective view of a filter according to an embodiment.

Referring to FIG. 1, a preferred embodiment of the filter 1 is illustrated in a perspective view. This embodiment of a filter includes a first hub 12, anchor members 30 projecting from the first hub 12 each having a hook 40, a second hub 14 connected to the first hub 12 by a connector 13, and a filter basket 50 coupled to the second hub 14. Locators 20, which position the filter 1 in the center of the blood vessel, may be coupled to the first hub 12 or provided as part of the filter basket 50. These locators 20 are preferably a part of the filter basket 50, as shown in FIG. 1.

The filter 1 may be made from any combination of suitable bio-compatible materials, such as, for example, polymer, memory polymer, memory metal, thermal memory material, metal, metal alloy, or ceramics. The anchor members 30 and filter members 51, 52 and 56 can be made from a plurality of elongate wires, which are preferably metal such as the Cobalt-Chromium-Nickel alloy known as Elgiloy®, and more preferably a super elastic shape memory alloy, such as Nitinol. The shape memory alloy can further be defined as preferably having an austenite finish (Af) temperature below body temperature. Nitinol is a low modulus material that allows the anchor and filter members of the filter to have low contact forces and pressures while still achieving sufficient anchoring strength to resist migration of the device within a blood vessel. As used herein, "wire" refers to any elongated member of narrow cross section, including rods, bars, tubes, ribbon and narrow sections cut from thin plate, and is not intended to limit the scope of the invention to elongated members of circular cross section, cut from wire stock or manufactured according to a particular method of metal forming. Although the filters of the various embodiments are preferably formed from a temperature-responsive shape memory material, such as Nitinol, they can also be formed of a compressible spring metal such as stainless steel, Elgiloy®, or a suitable plastic.

Anchor members 30 have a proximal end coupled to the first hub 12 and a distal end formed into or coupled to a hook 40. The anchor members 30 may be held together on their proximal ends at the first hub 12 by any of a number of suitable connection techniques, such as, for example, welding, laser welding, plasma welding or being bonded together. The first hub 12 may be hollow or have an interior space into which the proximal ends of the anchor members 30 may be inserted prior to bonding, such as by brazing, welding (preferably plasma welding) or gluing with a biocompatible adhesive.

Figure 2:
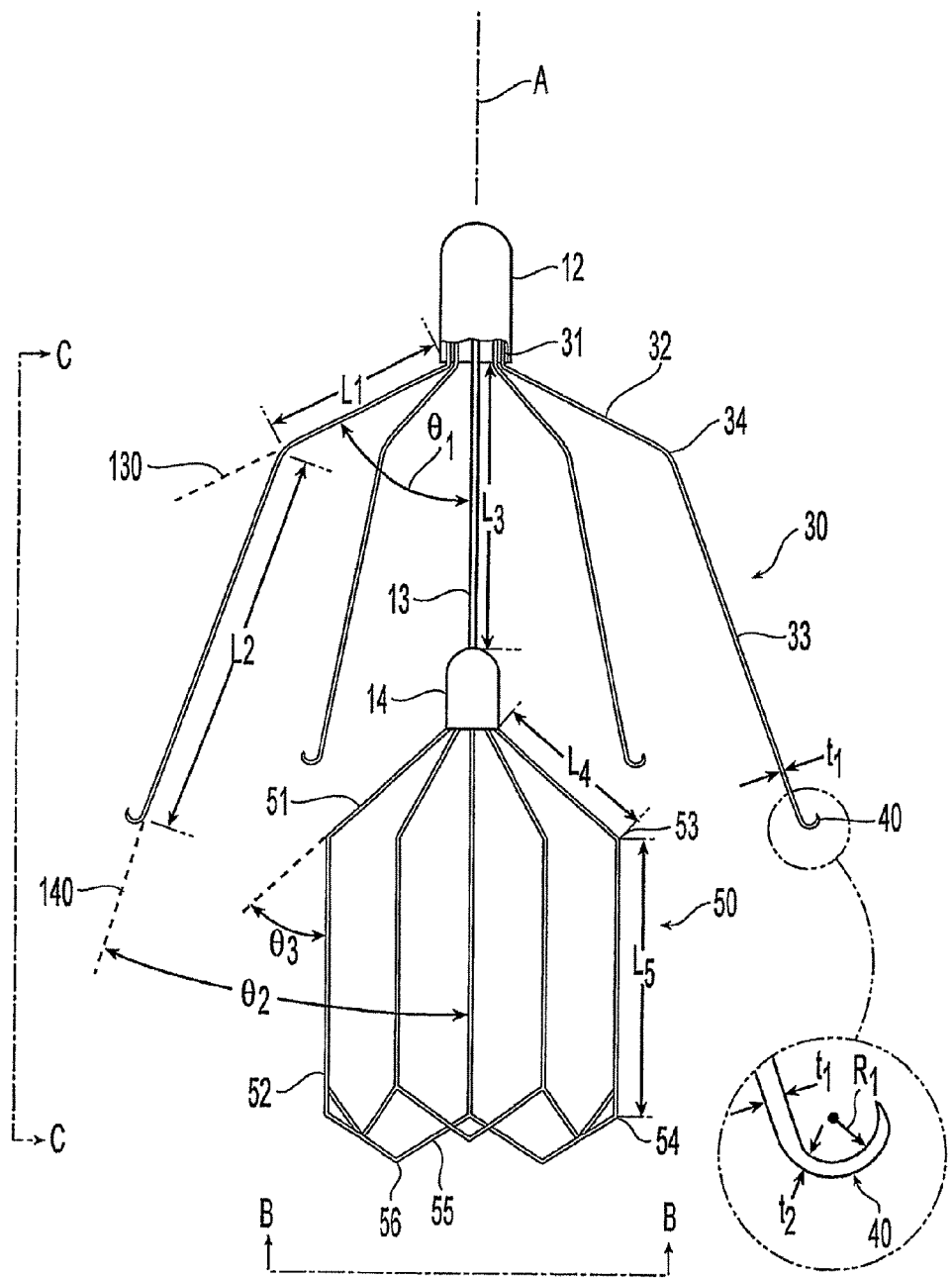
FIG. 2 is a side view of the filter of FIG. 1 viewed along A-A.

For illustration purposes only, FIGS. 1 and 2 show four anchor members 30. But fewer or more anchor members 30 may be used. For example, a minimum of three anchors may be used to ensure that the filter 1 is centered in the blood vessel. Alternatively, a filter 1 with six or more anchor members 30 positions the anchor members close enough together for them to function as a second filter basket.

Referring to FIG. 2, each of the plurality of anchor members 30 preferably include a first anchor segment 31 connected via a bend to a second anchor segment 32, which may be connected to a third anchor segment 33 via another, end 34. In a preferred embodiment, the third anchor segment 33 is connected to a hook 40 or bent into a hook 40. In other embodiments, the anchor members 30 may include fewer or more segments.

As shown in FIG. 2, a portion of first anchor segment 31 is disposed within the hub 12 and may be welded, brazed or otherwise coupled to other anchor members within the first hub 12. First anchor segment 31 preferably includes a first bend oblique with respect to the longitudinal axis A, which provides the linkage between the first and second anchor segments. The second anchor segment 32 may extend along axis 130 oblique with respect to the axis A at an angle $\theta_1$ with respect to the longitudinal axis A. The third anchor segment 33 extends along axis 140 oblique with respect to the longitudinal axis A at an angle $\theta_2$. The second anchor segment 32 may have a length $L_1$ measured along axis 130 from the first hub 12, and the third anchor segment 33 may have a length $L_2$ measured along axis 140 from bend 34. The thickness of anchor member 30 is nominally $t_1$. Where the anchor member 30 is a wire of circular cross section, the thickness $t_1$ of the anchor 30 may be the diameter of the wire. As shown in the detail in FIG. 2, the hook 40 may be contiguous to a plane and characterized by a radius of curvature $R_1$. The hook 40 has a diameter or thickness $t_2$, which may be less than the thickness $t_1$ of the rest of the anchor member 30. The anchor members 30, in their expanded configuration illustrated in FIGS. 1 and 2 (i.e., unconstrained in the high temperature form), are at a slight angle to the blood vessel wall, preferably within a range of from ten to forty-five degrees, to present the hooks 40 in an orientation that facilitates penetrating the vessel wall in order to secure the filter 1 within the vessel.

In another embodiment, the filter basket 50 can be configured to expand to an outer diameter greater than the inside diameter of a host blood vessel and the connector 13 can be configured to facilitate detaching hub 12 from hub 14.

Due to the larger size of the filter basket in this embodiment, the filter basket would tend to be adhered to the vessel wall via tissue ingrowth, thereby allowing the anchor members 20 and hub 12 to be removed from the blood vessel by disconnecting hub 12 from hub 14 while leaving the filter basket permanently in place. Preferably, the connector 13 can be configured as a bio-resorbable material or a suitable, detachable coupling means so that the connector 13 may be disconnected from hub 14.

The aforementioned filter and anchor member dimensions may be adjusted to accommodate inserting, locating or positioning, and securing of the filter 1 into blood vessels of varying diameters. The dimensions are preferably selected so that, when placed in the vessel, the hooks 40 press against the walls of the vein or vessel with sufficient radial force to ensure that the hooks engage the wall but not so much force as to cause injury to the wall. For example, a filter intended to be placed in a narrow vein or vessel, such as a child or canine vena cava, may have smaller dimensions than a filter intended to be placed in a large vein or vessel, such as an adult vena cava or femoral vein.

In an exemplary filter embodiment suitable for an adult human vena cava, when the filter 1 is at the temperature of the subject and unconstrained, the length of the second anchor segment 32 may be about 0.5 inches; the length of the third anchor segment 33 may be about 0.8 inches; the first angle $\theta_1$ may be about 20 degrees to about 90 degrees; the second angle $\theta_2$ may be about 0 degrees to about 60 degrees; the thickness $t_1$ of the anchor member may be about 0.013 inches; the thickness $t_2$ of the hook 40 may be about half the thickness $t_1$ of the anchor member 30; and the hook may have a radius $R_1$ of about 0.030 inches. In a preferred embodiment, the anchor member 30 has a cross sectional area of about 0.00013 squared inches, and the hook 40, particularly the curved section, has a cross sectional area of about 0.000086 squared inches.

The size (i.e., radius and thickness) of the hooks 40 for migration resistance, as well as the number of anchor members 30, may be determined by calculating the force applied to each hook when the filter 1 is fully occluded and the blood pressure in the vessel is allowed to reach 50 millimeters of mercury (mmHg). This force is approximately at least 70 grams on each anchor of a six-anchor device for at least 50 mmHg pressure differential in a 28 mm vessel. The desired total migration resistance force for an adult human vena cava filter is believed to be approximately 420 grams, and the load on the filter 1 would be correspondingly smaller in vessels of smaller diameter. To lower the maximum migration force that must be resisted by each hook, additional anchor members 30 with hooks 40 can be added to the filter 1.

It is preferable that the hooks 40 perform as an anchoring mechanism at a predetermined filter migration resistance force preferably defined as a function of a blood pressure range in the vessel, which is further preferably from about 10 mmHg up to about 150 mmHg. Having maintained its geometry at a predetermined filter migration resistance force within this range, the hook 40 preferably begins to deform in response to a higher force applied in the direction of the hubs, and releases at a force substantially less than that which would cause damage to the vessel tissue. The ability of the hook 40 to straighten somewhat allows the filter to be safely removed from the vessel wall. The migration force can be derived determined from a given pressure value using the following calculations, for example:

Since 51.76 mmHg=1.0 pounds per square inch (psi), $$50 \text{ mmHg} = 0.9668 \text{ psi};\qquad\qquad\text{Eq. 1.}$$

For a 28 mm vena cava:

$$A = \frac{\pi}{4}(28)^2 \text{mm}^2 = 615.4 \text{ mm}^2 = 0.9539 \text{ inches}^2;.\qquad\text{Eq. 2}$$

Migration force is calculated by:

$$P = F/A \quad F = P \times A \qquad\qquad\text{Eq. 3.}$$

$$0.9668 \text{ psi} \times 09539 \text{ inches}^2 = 0.9223 \text{ pounds} = 418.7 \text{ grams}.\qquad\text{Eq. 4}$$

Depending on the number of hooks 40, the required strength of each hook can be calculated. For a device with six hooks:

$$\text{Hook Strength} = \frac{\text{Filter Migration Resistance Force}}{\text{Number of Hooks}}.\qquad\text{Eq. 5}$$

$$= \frac{418.7}{6} = 69.7 \text{ grams}.\qquad\text{Eq. 6}$$

So each hook must be capable of resisting approximately at least 70 grams of force for the filter 1 to resist at least 50 mmHg pressure gradient in a 28 mm diameter vessel. In order to prevent or minimize excessive vessel trauma, each individual hook preferably has a low hook strength. By balancing the number hooks 40 and the individual hook strength, minimal vessel injury can be achieved while still maintaining the at least 50 mmHg pressure gradient criteria, or some other predetermined pressure gradient criteria within a range of about 10 mmHg to 150 mmHg.

Positioned upstream with respect to blood flow 8 from the anchor members 30 is a filter basket 50 oriented such that the basket opening faces away from the anchor members 30. In the embodiment illustrated in FIG. 1, the filter basket 50 is preferably coupled to a second hub 14 which itself is coupled to the first hub 12 by a connector 13. It should be noted that the second hub 14 and connector 13 are included in some but not all embodiments, and thus are optional elements.

The connector 13 connects the first and second hubs 12, 14 at a separation distance L3. The connector 13 is preferably strong and stiff enough to transmit compression force-such as may occur during filter delivery and operation-from the second hub 14 to the first hub 12 without buckling, and the connector 13 may also be flexible enough to permit the filter basket to move radially (i.e., to swing) about the longitudinal axis A when the filter 1 is secured within the blood vessel. The separation distance $L_3$ may range from no separation (i.e., the first and second hubs 12, 14 are contiguous) to about 1 inch. Nominally, the separation distance $L_3$ is sufficient to permit the anchor members 30 to deploy within the blood vessel and to provide sufficient flexibility for the filter basket 50 to swing the desired amount within the blood vessel. The connector 13 may be a single member, such as thick wire or tube, or a number of thin wires. The connector 13 can be constructed of a variety of biocompatible materials, including but not limited to stainless steel, Elgiloy®, or Nitinol. In an embodiment, the filter 1 is delivered by pushing it through a catheter with a push rod which presses on the second hub 14. In this embodiment, the connector 13 is sized to transmit the pushing force applied by the push rod from the second hub 14 to the first hub 12 without buckling. The connector 13 is also sized to withstand, without buckling, the force 10 applied by blood flow through the vessel in the situation where the filter basket 50 fills and maximum blood pressure is assumed at or near the filtration site. For example, referring to equations 1-6, the connector 13 of a filter intended for placement in an adult vena cava should be configured to resist at least 418.7 grams in compression without buckling.

In the embodiment illustrated in FIGS. 1-13, the purpose and configuration of the second hub 14 is similar to that of the first hub 12. Specifically, the second hub 14 connects the filter members together at their proximal ends by any of a number of suitable connection techniques, such as, for example, welding, laser welding, or plasma welding, or being bonded together. The second hub 14 may be hollow or have an interior space into which the proximal ends of the filter members may be inserted prior to brazing, welding (preferably by plasma welding) or gluing with a biocompatible adhesive.

In the embodiment of the filter basket 50 illustrated in FIGS. 1-7, the basket is formed by filter members that include a first segment 51, a second segment 52 and a retainer member 55. According to this embodiment, as shown in FIG. 2, the first segment 51 of each filter member is preferably coupled (e.g., by brazing, welding or gluing) to the second hub 14 on a proximal end and to the second segment 52 on its distal end in a joint or bend 53. The second segment 52 is further coupled to the retainer member 55 by joint 54. The retainer member 55 connects to each of the distal ends of the second segments 52, as illustrated in FIG. 3A.

In this embodiment, the first segments 51 of the filter basket member extend radially outward from the second hub 14 at an angle $\theta_3$ from the longitudinal axis A with a length $L_4$. The first segments 51 therefore generally define the bottom, with respect to blood flow, of the filter basket 50 and provide the filter members for capturing emboli flowing into the basket. In designing a filter for a particular blood vessel, the angle $\theta_3$ and length $L_4$ of the first segments 51 are selected so that the diameter DF of the filter basket 50 is less than the internal diameter of the blood vessel. In a preferred embodiment, angle $\theta_3$ ranges from approximately 90 degrees to approximately 20 degrees, and more preferably between approximately 80 degrees and approximately 45 degrees, and the length $L_4$ ranges from approximately 0.2 inches to approximately 0.6 inches.

In this embodiment, the second segments 52 of the filter members have a length $L_5$ preferably extending generally parallel to the longitudinal axis A. In alternative embodiments, the second segments 52 may be oriented at an orthogonal angle to the longitudinal axis, so the filter basket 50 forms a frustum. At their distal ends (i.e., upstream with respect to blood flow), the second segments are coupled to the retainer member 55 by any suitable connection, including welding, brazing, gluing and/or wrapping the second segments 52 around the retainer member 55. The second segments of the filter basket 50 define the volume of the filter basket for retaining emboli. Thus, the filter basket can be designed to capture and retain more emboli by increasing the length $L_5$ of the second segments 52, without changing the anchor member 30 configurations (which could impact their ability to engage the blood vessel wall).

Figure 3A:
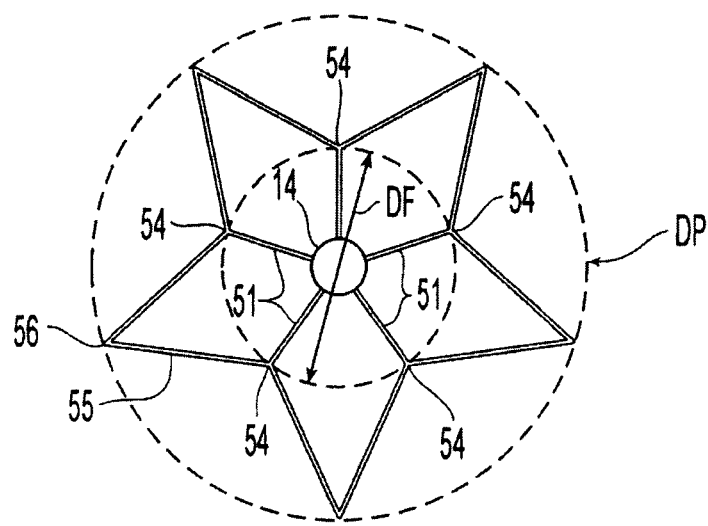
FIG. 3A is an end view of the filter of FIG. 2 viewed along B-B.
Figure 3B:
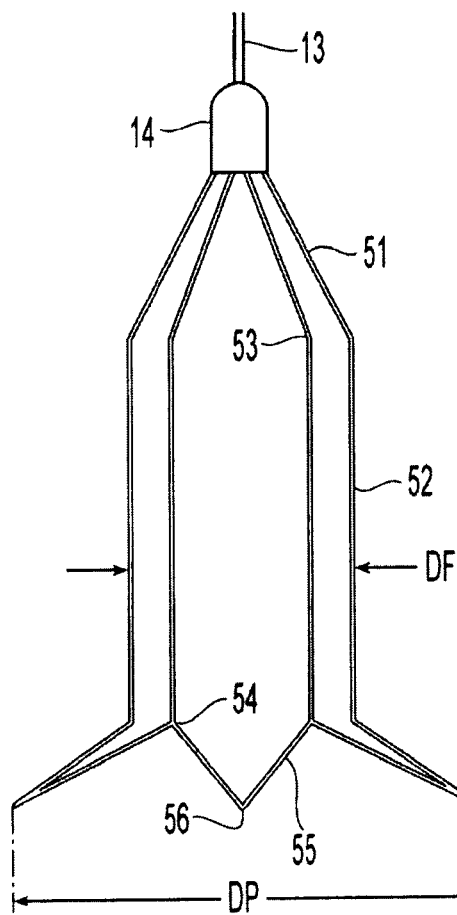
FIG. 3B is a side view of the filter basket of the filter shown in FIG. 2 viewed along C-C.

The retainer member 55 provides circumferential restraint to the second segments 52, thereby preventing radial expansion of the filter members when the filter basket 50 fills with emboli. Additionally, in the embodiment illustrated in FIGS. 2, 3A and 3B, portions of the retainer member 55 extend radially outward from the longitudinal axis beyond the circumference of the second segments 52 to form positioning pads 56. Referring to FIGS. 3A and 3B, the retainer member 55 extends at an oblique angle to the longitudinal access and radially outward to form the positioning pads 56 spanning positioning diameter DP, which may be set to be approximately equal to the internal diameter of the blood vessel. The positioning pads 56 may be provided with a suitable retention member such as, for example, the hook 40 shown and described herein.

Viewed end on, the retainer member 55 has a star shape as illustrated in FIG. 3A. By extending further from the filter longitudinal axis than the rest of the filter basket 50 (i.e., diameter DP defined by the positioning pads 56 is greater that the diameter DF of the filter basket 50), the positioning pads 56 may contact the vessel wall to position the filter basket within the blood vessel. In the embodiment illustrated in FIGS. 1-7, the retainer member 55 preferably includes of a series of triangles, which may be formed by laser cutting a hollow tube or bending a single wire in the shape illustrated. But other forms are possible, including sine wave, interconnected or alternating arcs or alternating semicircles.

According to this embodiment, if blood pressure on emboli entrapped in the filter basket 50 applies a radial force against the second segments 52, this force is applied to the retainer member 55 at the joints 54. To the extent the retainer member 55 flexes under this force, the joints 54 will be pressed radially outward which will draw the positioning pads 56 radially inward (i.e., toward the longitudinal axis). Alternatively, the retainer member 55 may permit the filter basket 50 to expand radially outward slightly but sufficiently restrain the expansion so that the filter members do not press against the blood vessel wall. So if the filter basket 50 fills with emboli and blood flow through the filter 1 acts on the trapped emboli to produce a radial force that tends to expand the filter basket, the positioning pads 56 will not transfer this force to the vessel wall, and may actually pull back from the vessel wall.

In addition to the advantage of preventing a full filter from applying greater pressure to the vessel wall, this retainer member 55 embodiment provides blood flow paths around the filter basket, such as the area between adjacent positioning pads 56 and the circumference of the filter basket 50, that remain open even if the filter basket is filled with emboli. Moreover, since the filter basket opening is upstream from the anchor members 30, the filter basket removes emboli from the blood before they reach the anchor members where they might otherwise be captured and increase the pressure applied to the anchor members.

Figure 5:
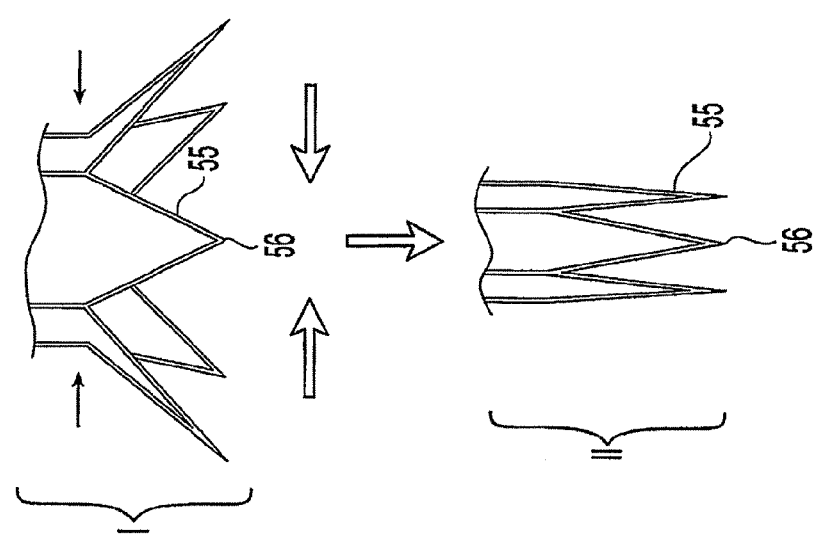
FIG. 5 is a detailed schematic view of a retainer member for the filter of FIG. 1 transforming from the configuration in FIG. 4B to the configuration of FIG. 6.

Referring to FIG. 5, the alternating triangle form of the retainer member 55 also facilitates folding of the filter basket during assembly so the filter can be fit into a catheter. As illustrated, the retainer member 55 will bend at each corner in an accordion fashion to significantly reduce its circumference and the positioning pads 56 can be bent inward. Preferably, the retainer member 55 is fabricated from a shape memory alloy, such as Nitinol. The memory shape of a retainer member according to this embodiment is preferably the expanded configuration I, as shown in FIG. 5. The retainer member can then be cooled and folded into its compressed configuration II for installation in a storage tube or catheter, as is also shown in FIG. 5. By folding in an accordion fashion, the retainer member 55 allows the filter basket to collapse into the narrow profile of FIG. 6 for positioning within a storage tube or catheter.

Although the embodiment illustrated in FIGS. 1-38 features five filter members, more may be employed to reduce the space between filter members in order to capture smaller emboli and/or to provide a larger filter basket 50 for use in a larger blood vessel. For example, FIGS. 3A and 38 illustrate an embodiment including eight filter members. A filter according to the embodiment may also have fewer than five filter members. Other features of the filter basket 50 may be consistent with those of the aforementioned embodiments.

Figure 7:
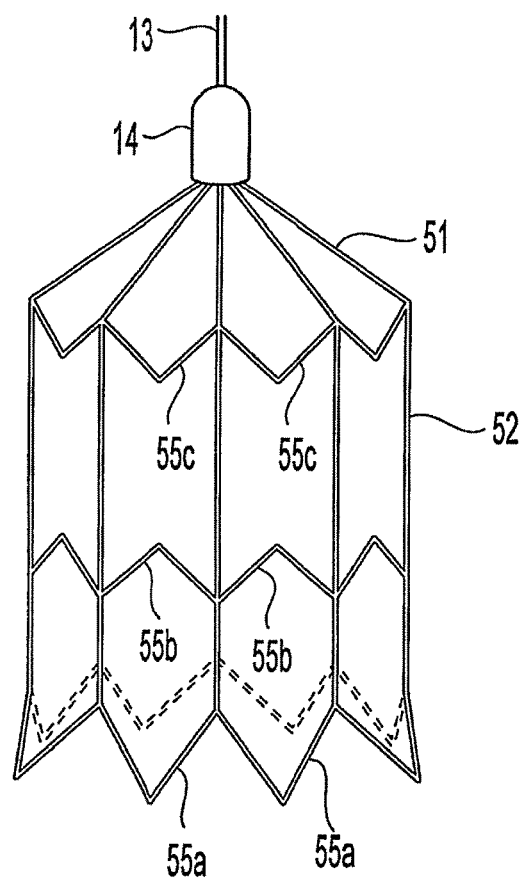
FIG. 7 is a side perspective view of another embodiment of the filter basket.

While the aforementioned embodiments include a single retainer member 55, additional retainer members may be used to provide more filter mesh elements for capturing emboli and/or additional lateral restraint to prevent expansion of the filter basket 50. For example, FIG. 7 illustrates an embodiment featuring three radial restraints, including retainer member 55A at the upstream end, retainer member 55B at an intermediate position, and retainer member 55C at or near the downstream end of the second segment 52.

Figure 8:
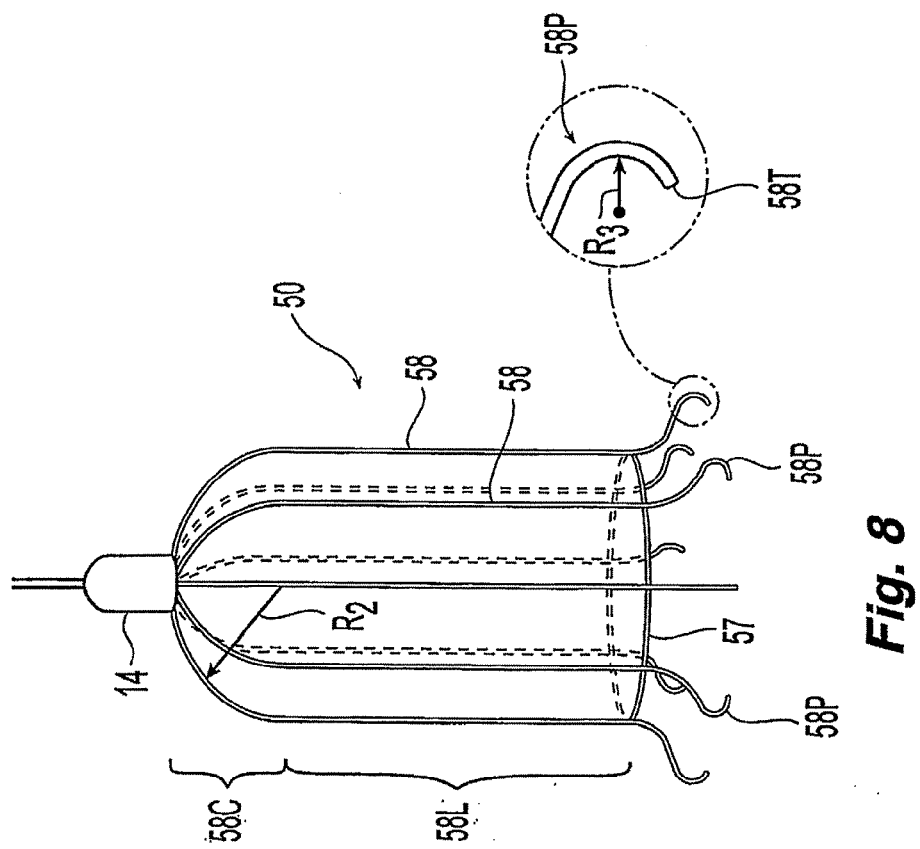
FIG. 8 is a side perspective view of yet another embodiment of the filter basket.

Another embodiment of the filter basket 50 is illustrated in FIG. 8. In this embodiment, the filter members 58 first extend radially outward from the second hub 14 so as to preferably bend through a radius $R_2$ in curved portion 58C to a linear portion 58L that is preferably approximately parallel to the longitudinal axis. Linear portion 58L couples to a retainer member 57 and bends radially outward to end in a pad portion 58P. The pad portion 58P, by extending radially outward from the filter basket 50, may contact the blood vessel wall to position the basket near the centerline of the vessel. A smooth portion for contacting the blood vessel wall can be provided on the pad portion 58P by bending the member through a tight radius $R_3$ so that the tip 58T points inward toward the longitudinal axis. Not all filter members 58 need to include a pad portion 58P, since the centering function may be accomplished by as few as three, preferably equiangularly spaced pad portions 58P. Radial expansion of the filter members 58 due to pressure from captured emboli will not result in increased pressure on the blood vessel wall because the retainer member 57 prevents the pad portions 58P from moving outwardly. This embodiment of the filter basket 50 resembles a birdcage in its deployed configuration.

Figure 9:
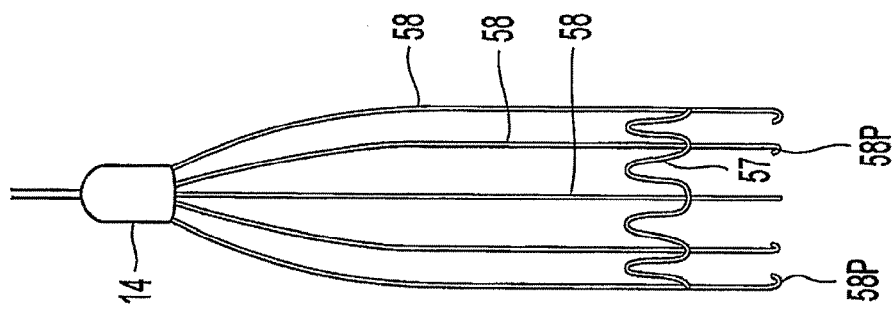
FIG. 9 is a side view of the filter basket of FIG. 8 in a folded configuration.

In order to fit the birdcage filter basket 50 embodiment into a catheter, the curved portion 58C and pad portions 58P of the filter members 58 are straightened and the retainer member 57 folds into a reduced circumference, such as by folding accordion style as illustrated in FIG. 9.

Figure 11:
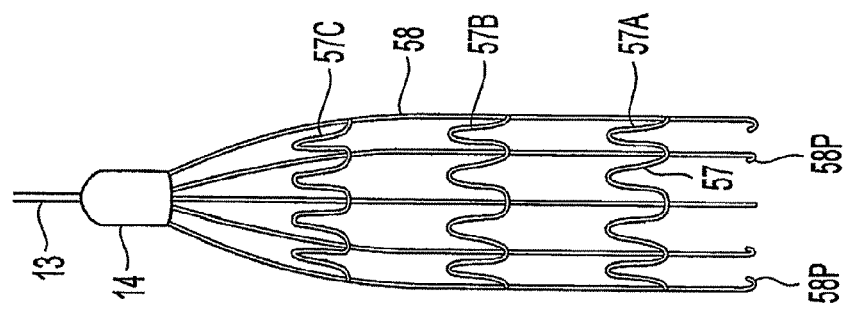
FIG. 11 is a side view of the filter basket of FIG. 10.
Figure 10:
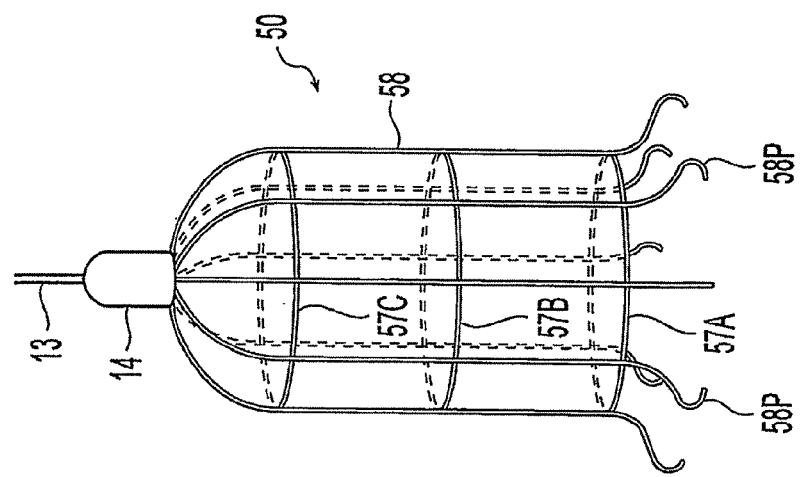
FIG. 10 is a side perspective view of another embodiment of the filter basket.

In an embodiment of the birdcage filter basket, multiple retainer members 57 may be employed, such as the three retainers 57A-57C illustrated in FIG. 10. In order to fit this embodiment into a catheter, each of the retainer members 57A-57C fold into a reduced circumference, such as by folding accordion style as illustrated in FIG. 11.

An alternative embodiment of the birdcage filter basket 50 may be formed by employing a retainer member 55, such as illustrated in FIG. 5, which includes positioning pads 56 that are preferably pointed and extend radially beyond the diameter of the filter basket. With the positioning pads 56 able to center the filter basket 50 in the blood vessel, the pad portions 58P of the filter members 58, such as are shown in FIGS. 8 and 10, may be eliminated in this embodiment.

Figure 12A:
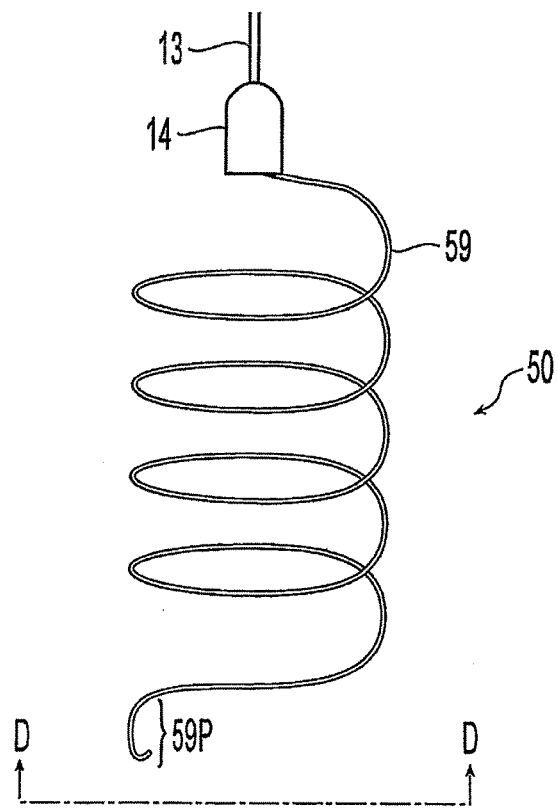
FIG. 12A is a side perspective view of yet another embodiment of the filter basket.
Figure 12B:
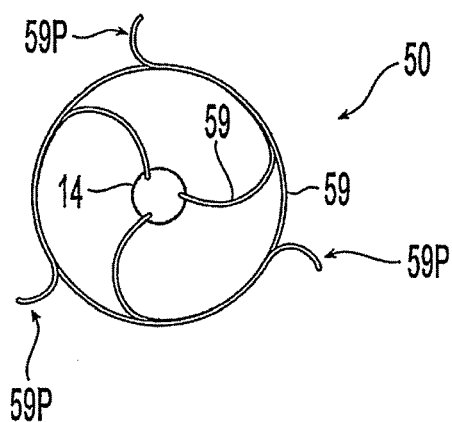
FIG. 12B is an end view of another embodiment of the filter.

Yet another embodiment of a filter basket 50 is illustrated in FIG. 12A. In this embodiment, the filter members 59 are formed in a helical shape. The proximal ends of the filter members 59 are coupled to the second hub 14 and the distal ends are formed into a pad portion 59P. For clarity, FIG. 12A shows only a single helical member 59, but more helical members 59 may be used. For example, FIG. 12B shows a three-member filter basket 50 from view D-D. But even more members 59 may be employed. When multiple helical members 59 are employed, they are oriented on the second hub 14 equiangularly about the longitudinal axis in order to present a tight mesh of filter members 59. For example, FIG. 12B shows three members 59 spaced 120 degrees apart about the longitudinal axis.

The pad portion 59P on the distal end of each filter member 59 is formed by first bending the member radially outward away from the longitudinal axis (as shown in FIG. 12B) and then back toward the longitudinal axis (as shown in FIG. 12A). By extending beyond the diameter of the filter basket 50, the pad portion 59P may contact the blood vessel wall in order to position the basket near the vessel's centerline.

In order to fit the helical embodiment into a catheter, the filter members 59 can be straightened and/or wound more tightly into a longer, tighter helix. Once the filter warms to body temperature, the filter members 59 will resume the helical form as illustrated in FIG. 12A.

Figure 13:
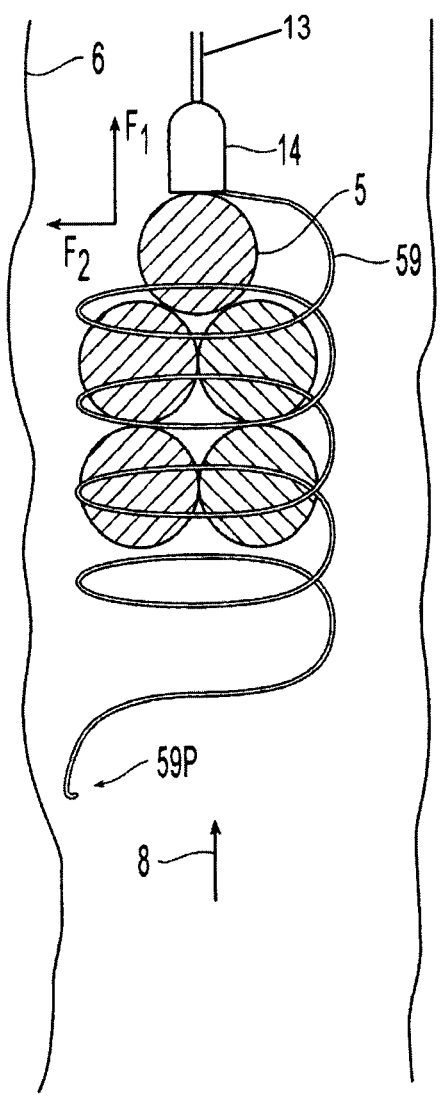
FIG. 13 is a side perspective view of the filter basket of FIG. 12A disposed in a blood vessel.

Due to their helical shape, pressure on the filter members 59 by entrapped emboli does not lead to increased stress on the blood vessel walls. As illustrated in FIG. 13, pressure on the emboli 5 from blood flow 8 will be transferred primarily toward the second hub 14 via a longitudinal force component $F_1$. To the extent there is a radial force component $F_2$, this force is accommodated by the helical members 59 expanding their diameters while contracting in length parallel to the longitudinal access. Thus, there is no lever mechanism applying additional pressure to the blood vessel wall.

Figure 14:
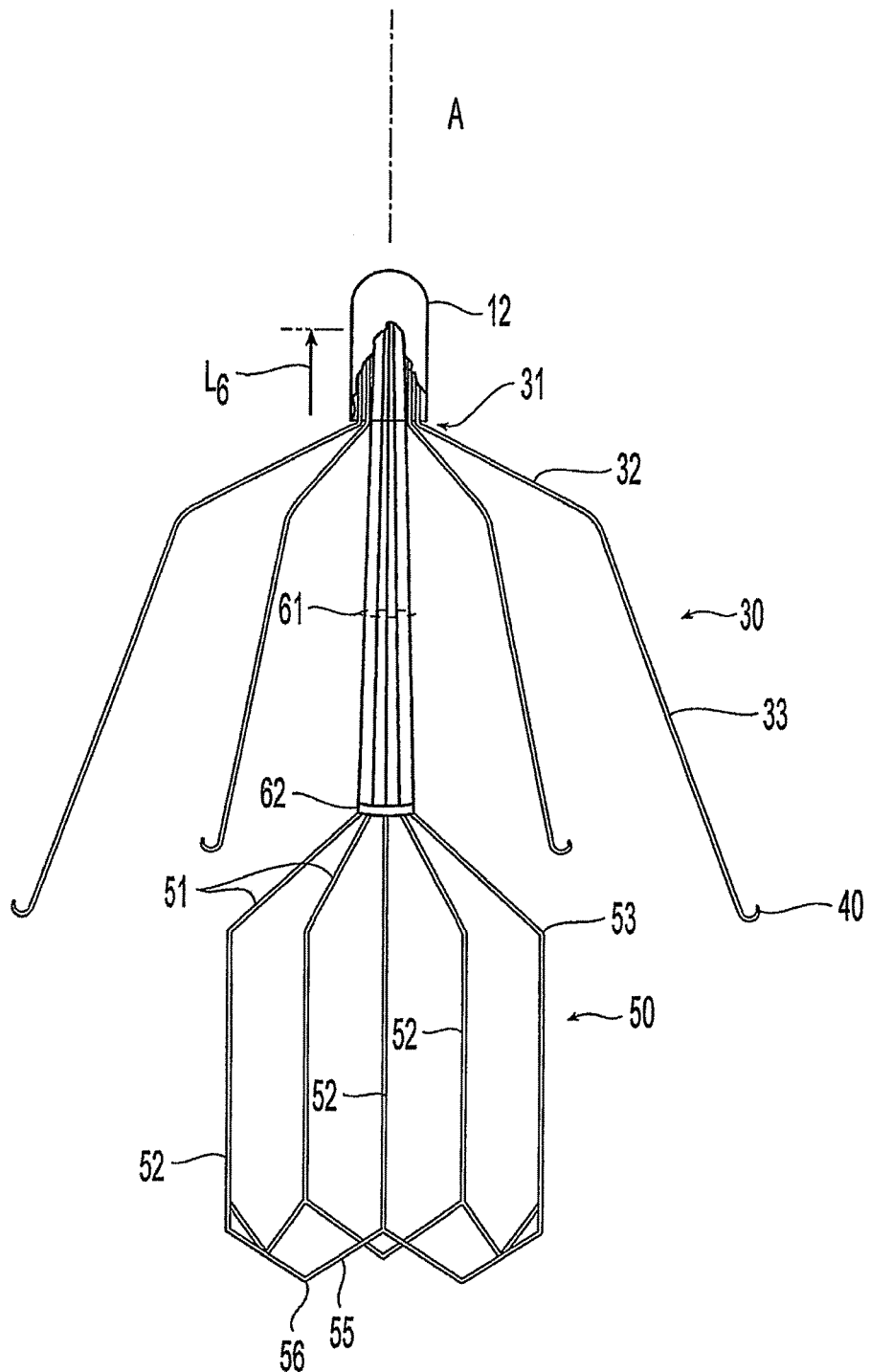
FIG. 14 is a side perspective view of another preferred embodiment of the filter.

While the foregoing embodiments include a second hub 14 and an inter-hub connector 13, these structures are not essential to providing a filter basket that will not apply additional pressure to the blood vessel wall or block blood flow when filled with emboli. For example, FIG. 14 illustrates an embodiment which replaces these structures by extending the filter members with an extended section 61. In this embodiment, the extended section 61 separates the filter sections 51, 52 of the filter members from the hub 12 and anchor members 30. Each filter basket extended section 61 is coupled to the first section 51 by a bend or weld and extends generally parallel to the longitudinal axis for a length L6 to its proximal end. The proximal end of the extended sections 61 may be inserted into and coupled to (e.g., by welding, brazing or gluing) the hub 12 to hold the ends together. The length L6 of the extended sections 61 may be sufficient to place the filter basket 50 upstream (with respect to blood flow) from the anchor members 30 to help facilitate deployment of the filter in the blood vessel without the filter and anchor members becoming tangled. Additionally, the length of the extended section 61 gives it flexibility so the basket can move (i.e., swing) within the blood vessel to allow the filter basket to seek the blood vessel centerline and avoid applying undue pressure to a point or portion of the blood vessel wall. The embodiment of FIG. 14 can be provided with anchor members (not shown) coupled to the distal end of the basket 50 proximate the pad points 56. The feature of anchor members connected to the pad points 56 is believed to alleviate pressure applied against the hub 12 as long as such anchor members do not expand radially outward.

In the embodiments illustrated in FIG. 14, pressure applied by emboli captured in the filter basket may cause the extended sections 61 to expand radially. But this movement will not result in greater pressure being applied to the blood vessel wall because the retainer member 55 prevents expansion of the distal end of the filter member 52. Thus, additional retainer members are not required with this embodiment. Nevertheless, this embodiment may be combined with the multiple-retainer embodiments illustrated in FIGS. 7 and 10. Also, in an alternative embodiment, the extended sections 61 may be held together by a band 62 positioned a distance from the hub 12, such as in the vicinity of the bend joining the extended sections 61 with the first sections 51. The band 62 may be any bio-compatible material and may be joined to the extended sections 61 by welding, brazing, or gluing. Alternatively, the band 62 may not be a separate piece, and instead may be formed by welding, brazing or gluing the extended sections 61 together.

Figure 4A:
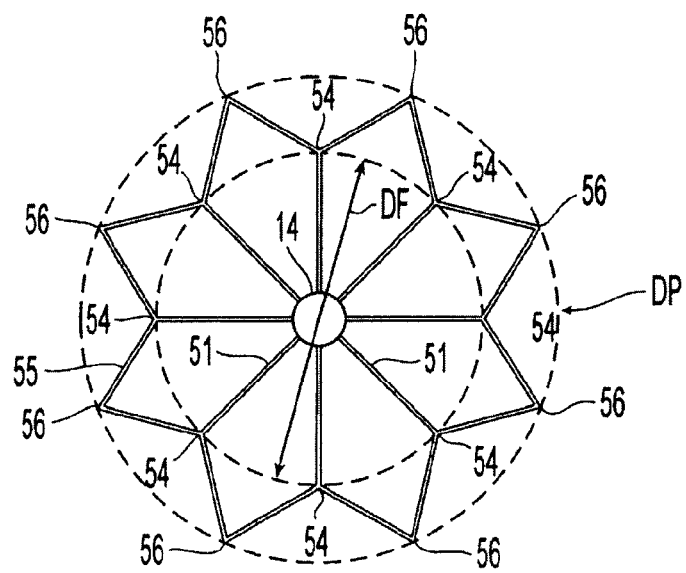
FIG. 4A is an end view of another embodiment of the filter basket.
Figure 4B:
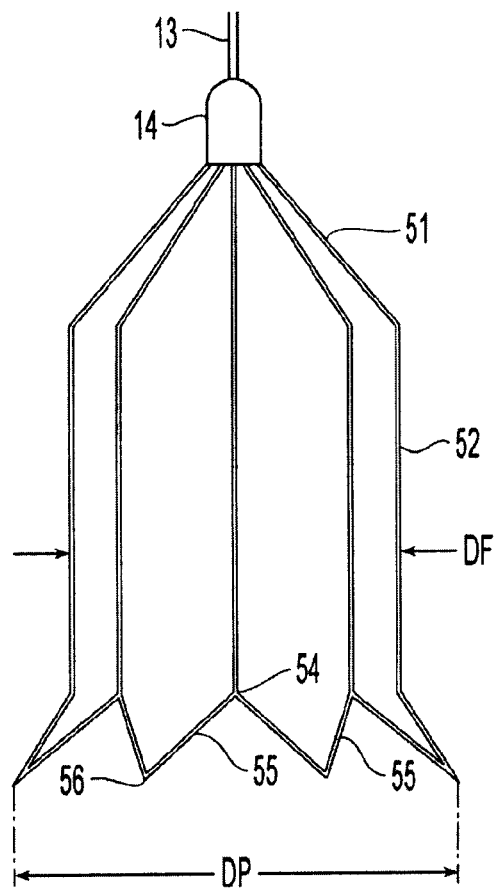
FIG. 4B is a side view of the filter basket of FIG. 4A.
Figure 6:
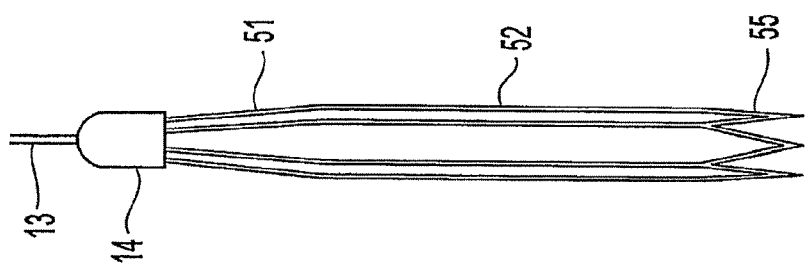
FIG. 6 is a side view of the filter basket of the filter shown in FIG. 1 in a folded configuration.

In the embodiment illustrated in FIG. 14, the filter members and filter basket may be constructed using any of the techniques described above with respect to the foregoing embodiments. So the filter basket may include more filter members as illustrated in FIGS. 4A and 4B, or be one of the birdcage embodiments illustrated in FIGS. 8-11. The helical filter basket embodiment illustrated in FIGS. 12A and 12B may also be employed, particularly in combination with a band 62 positioned above the start of the helical form to hold the helixes in longitudinal alignment.

FIG. 14 also illustrates an embodiment of a hollow hub 12. In this embodiment, the first anchor segments 31 and extended filter members 61 are inserted into the hollow hub 12 for bonding. In this embodiment, the hub 12 provides lateral support for the first anchor segments and extended filter member sections 31, 61. This may permit the filter members to experience greater bending force than embodiments in which the members are welded to an end surface of the hub, which is advantageous for embodiments that feature filter members, like the extended filter sections 61 that are subject to bending in service. This embodiment enables a number of assembly alternatives. The first anchor segments and extended filter member sections 31, 61 may be welded together and then covered by and bonded to the hub 12. Alternatively, these components 31, 61 may be first inserted into the hub 12 and then welded to each other and to the hub. Alternatively, the components 31, 61 may be first inserted into the hub 12 and then brazed together and to the hub. Alternatively, the components 31, 61 may be first inserted into the hub 12 and then glued together and to the hub with a bio-compatible adhesive.

The various embodiments feature a filter basket 50 that is positioned upstream with respect to blood flow 8 from the anchor members and that does not include hooks or other anchoring structure. Thus, the filter basket floats in the blood vessel upstream from the anchoring structure. Radial positioning structures, such as generally pointed positioning pads 56, and/or generally curved pad portions 58P, 59P help the filter to locate (float) near the centerline of the blood vessel without applying undue stress to the walls. This configuration permits the filter basket to capture emboli without applying additional pressure to the blood vessel walls when the filter fills with emboli.

The use of a thermal shape memory material, such as Nitinol, for the anchor and filter members facilitates collapsing the filter radially inward from its normally expanded (i.e., unconstrained) configuration into a more compact configuration for insertion into a blood vessel.

By forming the anchor and filter members from a shape memory material or Nitinol alloy material, such as Nitinol wire, transition between the martensitic and austenitic forms of the material can be achieved by temperature changes above and below a transition temperature (referred to herein as the martensitic-to-austenitic transition temperature).

Using a shape memory material, such as Nitinol, the deployed shapes and configurations of the filter members can be set (i.e., imprinted with a memory shape) by annealing the members at high temperature while holding them in the desired shape. Thereafter, whenever the filter is in the austenitic form (i.e., at a temperature above the martensitic-to-austenitic transition temperature), the members return to the desired shape. Example methods for setting the high-temperature shape of filters are disclosed in U.S. Pat. No. 4,425,908, which is hereby incorporated by reference in its entirety.

By virtue of the characteristics of shape memory material, the anchor and filter members can be held in a collapsed, straight form that can pass through a length of fine plastic tubing with an internal diameter of approximately two millimeters (2 mm), e.g., a No. 7 French internal diameter catheter. In its high temperature form, the filter 10 recovers to a preformed filtering shape as illustrated in FIGS. 1, 2, 3B, 4B, 7, 8, 10, 12, 13, and 14. Alternatively, the anchor and/or filter members may be made of spring metal wires which can be straightened and compressed within a catheter or tube and will diverge into the filter shapes illustrated in the figures when the filter is ejected from a delivery catheter.

Figure 15:
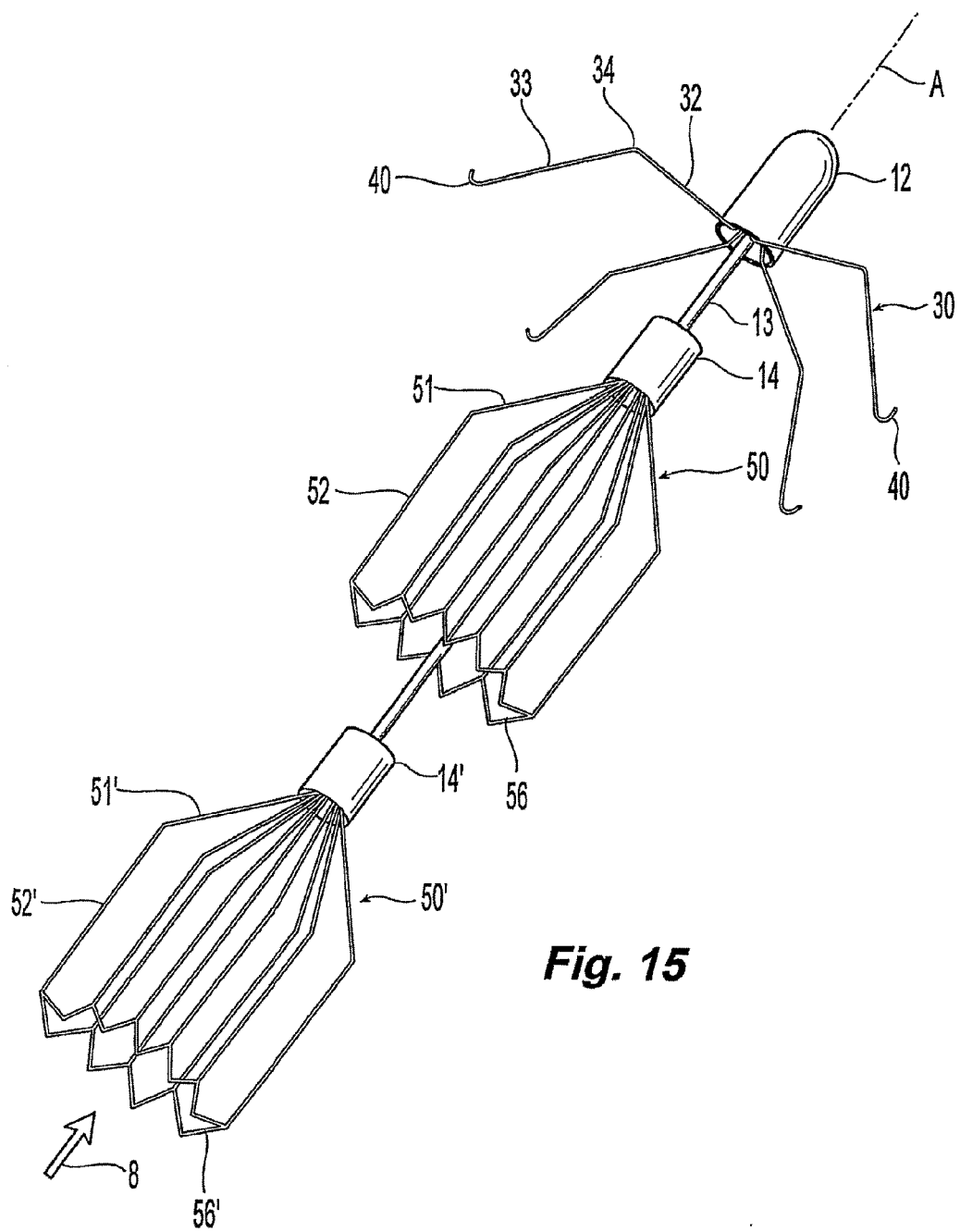
FIG. 15 is a side perspective view of yet another embodiment of the filter.
Figure 15A:
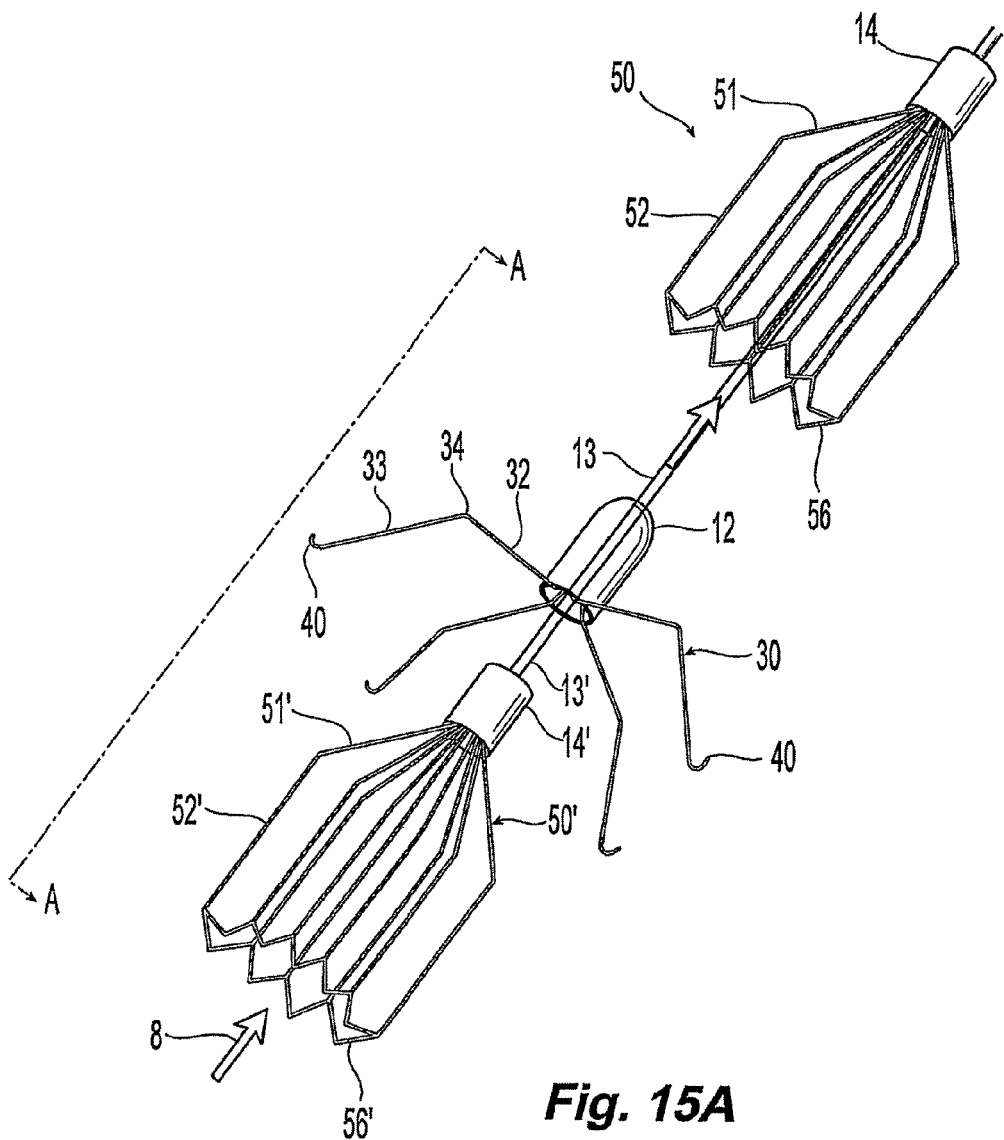
FIG. 15A is a side perspective view of another embodiment of the filter.
Figure 16:
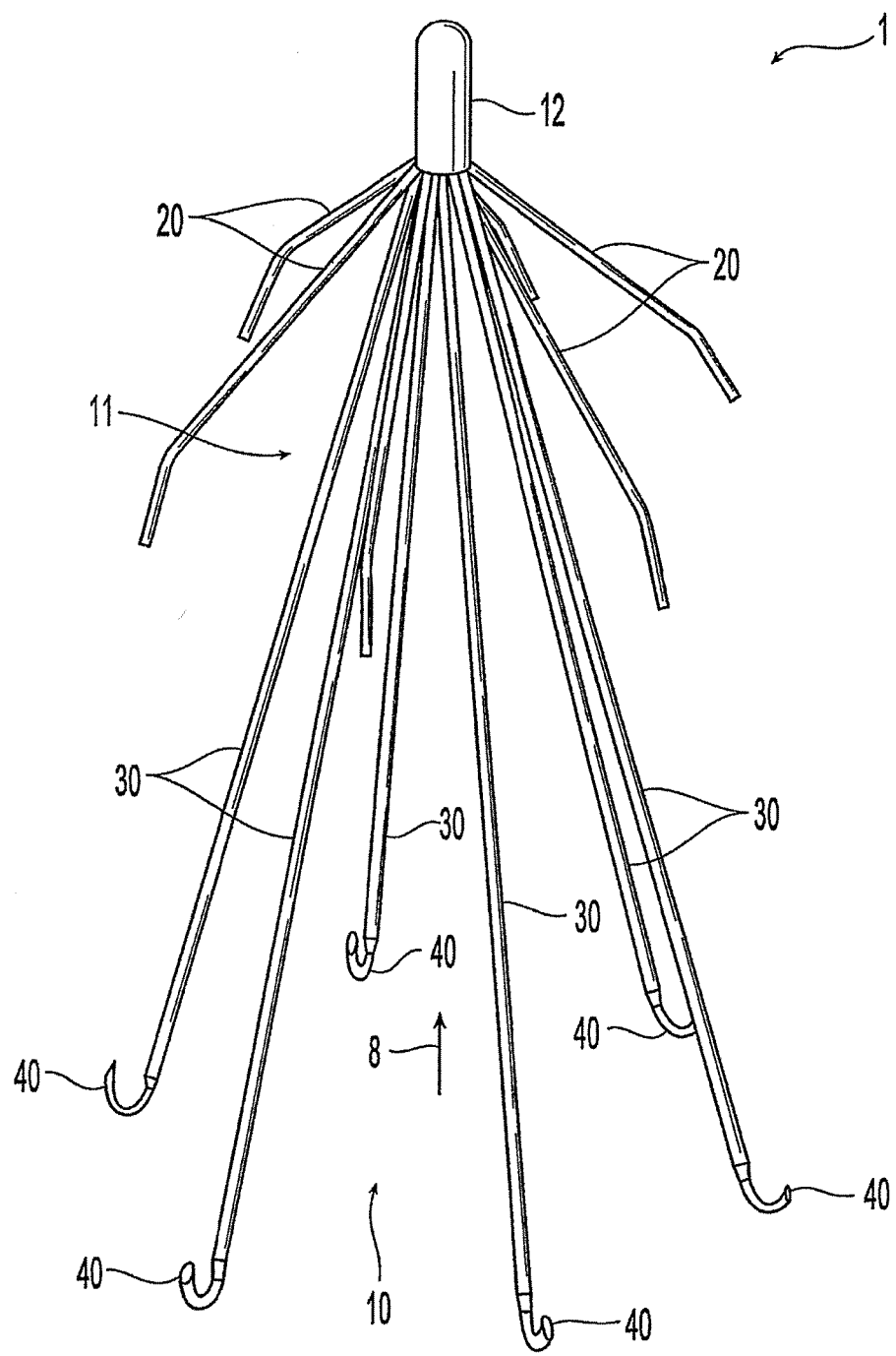
FIG. 16 is a perspective view of a known blood filter.
Figure 17:
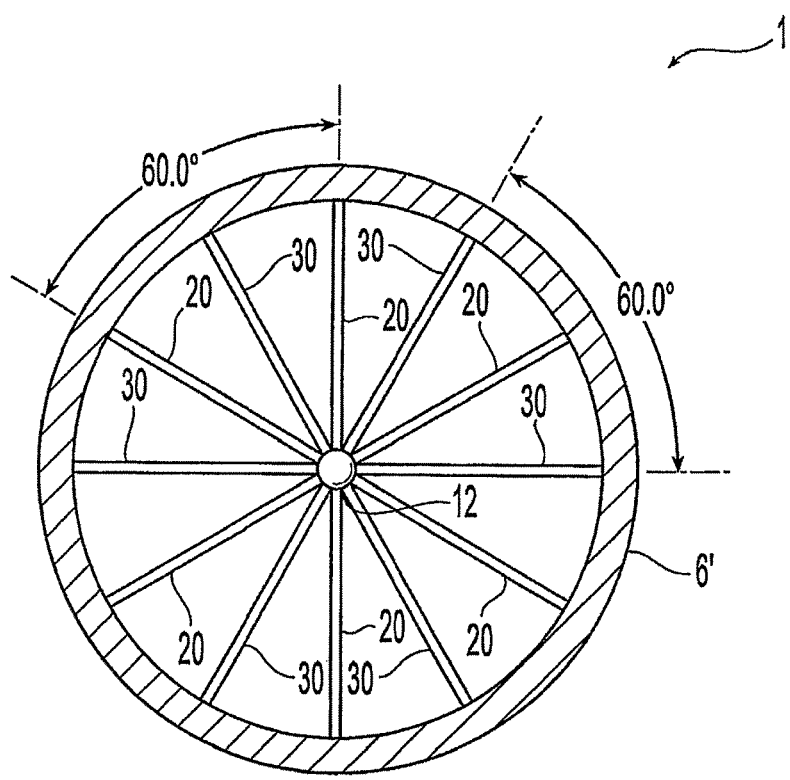
FIG. 17 is an end view of the filter shown in FIG. 16 implanted in a blood vessel.
Figure 18:
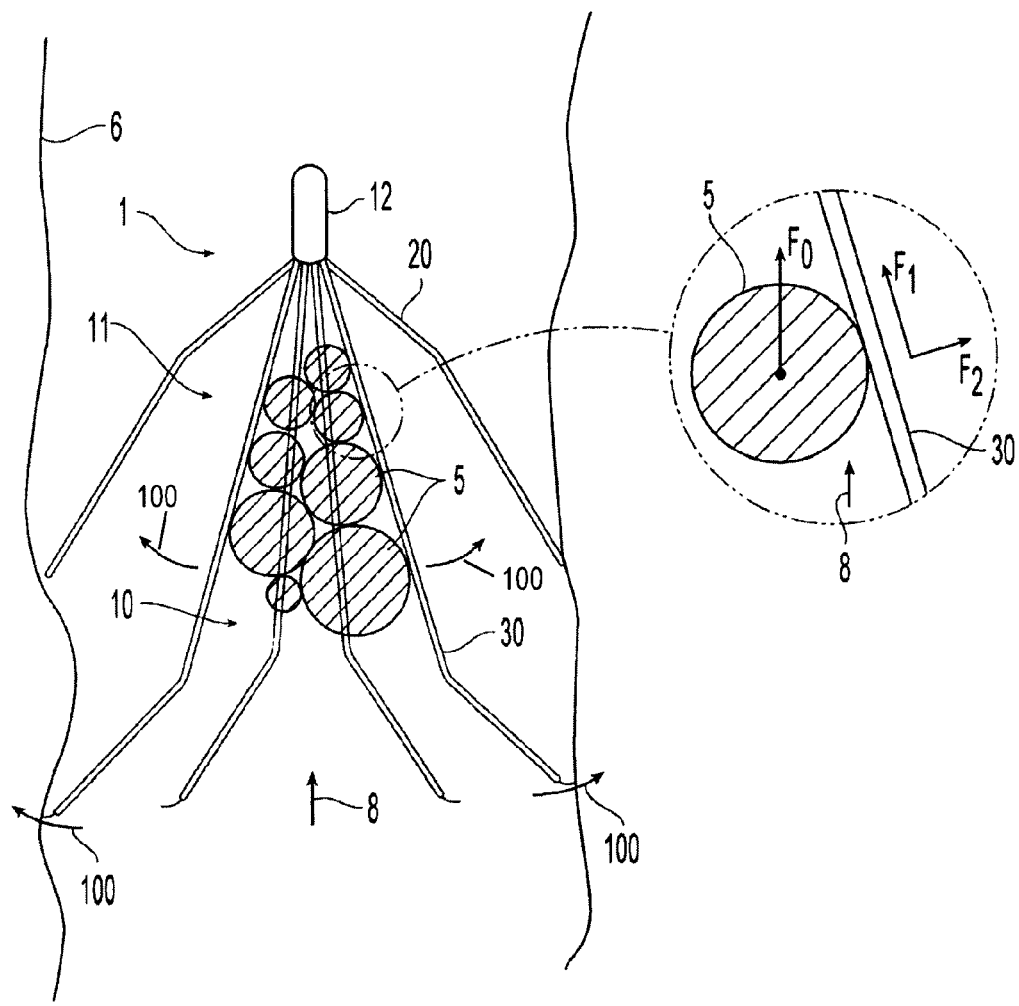
FIG. 18 is a perspective view of the filter shown in FIG. 16 implanted in a blood vessel.
Figure 19:
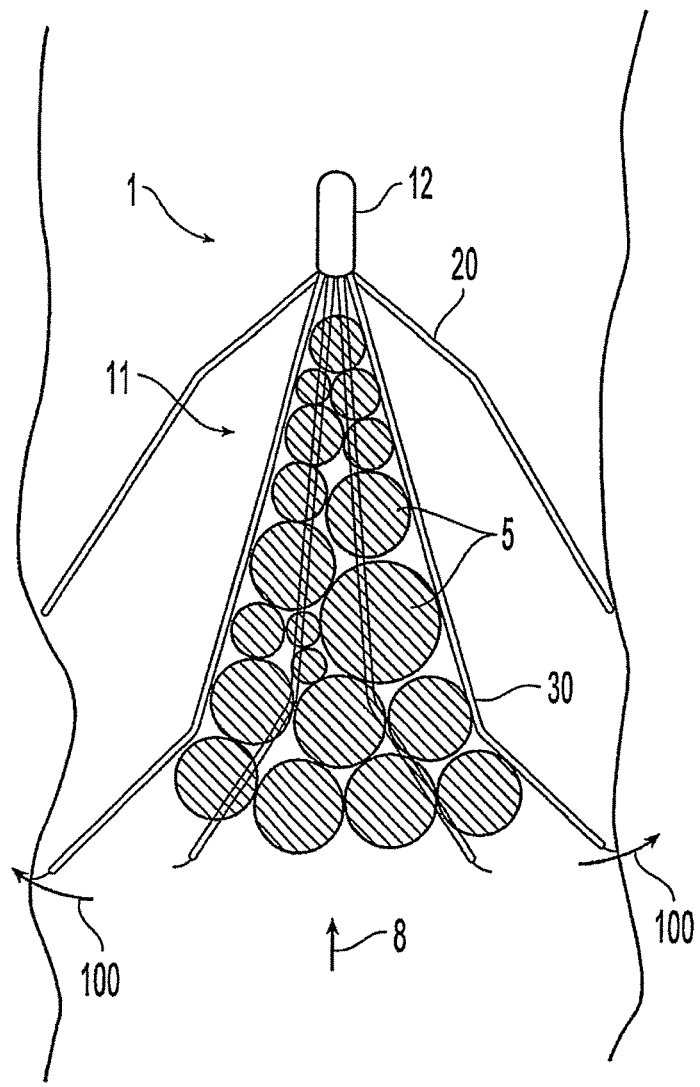
FIG. 19 is another perspective view of the filter shown in FIG. 16 implanted in a blood vessel.

FIG. 15 illustrates another embodiment of a filter which includes a second filter basket 50' positioned upstream from the first filter basket 50. The structure of the second connector 13' and second hub 14' are similar to those for the first connector 13 and first hub 14 described above. Further, the second filter basket 50' preferably includes filter elements 51', 52' and 56' which are preferably similar to those for the first filter basket 50 described above. The second filter basket 50' may be sized to be smaller in cross section than that of the first filter basket 50 so that the filtering of emboli is divided between the two filter baskets 50, 50'. In the second filter basket 50', the number of filter members 51' and 52' can be configured to provide for an open area ratio larger than an open area ratio of the first filter basket 50 so that blood clots that pass through the second basket (which has a larger open area ratio) are captured downstream by the first filter basket 50 (which has a smaller open area ratio). In the preferred embodiment, the open area ratio of the second filter basket 50' can be at least 20:1 while the open area ratio of the first basket can be at least 10:1. Hub 12 to which anchor members 30 are coupled may alternatively be placed between the first and second filter baskets, as is shown in FIG. 15A.

In another embodiment, the filter baskets may be formed from sheets of metal alloy or tubular stock, such as Nitinol, or plastic perforated with numerous holes. The holes in the sheets are sized and spaced to capture emboli and provide enough flow through the filter to prevent the formation of emboli and ensure sufficient filtering of the blood. In this embodiment, the sheets are joined along longitudinal folds so the filter sheets can be collapsed to a narrow profile for positioning within a catheter.

A filter 1 according to the various embodiments may be delivered to a blood vessel by a delivery unit such as, for example, the unit described in U.S. Pat. No. 6,258,026, which is incorporated by reference in its entirety. The filter 1 is delivered through a catheter or delivery tube to a generally centered position within a body vessel, as described in further detail in the above-mentioned patent. Further methods of delivering a blood filter suitable for use with the various embodiments are disclosed in PCT International Application No. PCT/US06117890, entitled "Embolus Blood Clot Filter and Delivery System," filed on May 9, 2006, which is hereby incorporated by reference in its entirety.

While the present invention has been disclosed with reference to certain preferred embodiments, numerous modifications, alterations, and changes to the described embodiments are possible without departing from the sphere and scope of the present invention. Accordingly, it is intended that the present invention not be limited to the described embodiments, but that it have the full scope defined by the language of the following claims, and equivalents, thereof.

What is claimed is:

1. A filter to be placed in a flow of blood through a blood vessel having a blood vessel wall, the filter comprising:
   a) a first plurality of circumferentially spaced apart filter members defining a first filter having a first diameter, a plurality of the filter members of the first plurality being anchor members configured to anchor the first filter to the blood vessel wall;
   b) a second filter in the form of a basket positioned upstream from and connected to the first filter, the second filter including a second plurality of circumferentially spaced apart filter members defining a second diameter that is smaller than the first diameter; and
   c) the second diameter being maintained by a plurality of retainer members that prevent outward radial movement of the second plurality of filter members so that blood can flow around the basket, in between the basket and the vessel wall; wherein the plurality of retainer members extend to a diameter smaller than the first diameter.

2. The filter of claim 1, wherein some of the first plurality of filter members are with hooks and some of the first plurality of filter members are without hooks.

3. The filter of claim 1, wherein the retainer members are each coupled to the second plurality of filter members and configured to prevent expansion of the second plurality of filter members.

4. The filter of claim 3, wherein the retainer members each comprise a portion that extends radially beyond the second diameter of the filter basket.

5. The filter of claim 3, further comprising a second plurality of retainer members coupled to the second plurality of filter members and configured to prevent expansion of the filter members of the second plurality; wherein the second plurality of retainer members extend to a diameter smaller than the first diameter.

6. The filter of claim 1, wherein at least one of the first plurality of filter members includes a portion that extends radially beyond the second diameter of the filter basket.

7. The filter of claim 1, wherein some of the filter members have a helical form.

8. A filter to be placed in a flow of blood through a blood vessel, the filter comprising:
   a) a first hub deposed along a longitudinal axis;
   b) a second hub coupled to the first hub and disposed along the longitudinal axis, spaced upstream from the first hub;
   c) a plurality of circumferentially spaced apart anchor members projecting from the first hub to define a first diameter, at least some of the anchor members including a hook configured to penetrate a wall of the blood vessel when the filter is positioned in the blood vessel;
   d) a filter basket having a filter basket opening, the filter basket coupled to the second hub and configured so that the filter basket opening faces away from the second hub;
   e) the basket having a plurality of filter members with one end being a proximal end that is attached to the second hub and another end being a free end that defines an end portion of the basket spaced farthest away from the first hub; and
   f) retainer members that disallow radial movement of the free ends of the filter members away from the longitudinal axis so that the all of the free ends do not contact the vessel wall, enabling blood to flow around the basket; wherein the filter members and retainer members extend to respective diameters smaller than the first diameter.

9. The filter according to claim 8, further comprising a connector coupling the first hub to the second hub.

10. The filter according to claim 8, wherein the plurality of filter members have a helical form.

11. The filter according to claim 8, wherein the retainer members include a first plurality of retainer members and a second plurality of retainer members that are spaced from the first plurality of retainer members, the second plurality of retainer members being coupled to the plurality of filter members and configured to limit radial expansion of the plurality of filter members; wherein the first plurality of retainer members and the second plurality of retainer members extend to respective diameters smaller than the first diameter.

12. The filter according to claim 11, wherein some of the first plurality of retainer members comprise a portion that extends beyond a diameter of the filter basket.

13. A filter to be placed in a flow of blood through a blood vessel having a blood vessel wall, the filter comprising:
   a) a first hub disposed along a longitudinal axis;
   b) a plurality of anchor members projecting from the first hub to a first diameter, at least some of the plurality of anchor members including a hook configured to penetrate the wall of the blood vessel when the filter is positioned in the blood vessel;
   c) a second hub connected to the first hub;
   d) a filter basket comprising a plurality of filter members and having a basket periphery that surrounds a basket opening into which blood can flow, each filter member including an extended section coupled to the second hub and at least one filter section, wherein the extended section is configured to position the filter section upstream from the second hub and the plurality of anchor members;
   e) wherein the plurality of filter members includes upstream end portions that are connected together circumferentially by retainer members that retard radially outward movement of the filter members, wherein the basket periphery is sized and shaped to allow blood flow around the filter basket;
and wherein the filter members and retainer members extend to respective diameters smaller than the first diameter.

14. The filter according to claim 13, further comprising a connector coupling the first hub to the second hub.

15. The filter according to claim 13, wherein the filter basket is connected to the plurality of anchor members by a bio-resorbable member so that the filter basket is separable from the anchor members after a predetermined time period subsequent to implantation of the filter in the blood vessel.

16. The filter according to claim 13, further comprising a retainer member coupled to each of two adjacent filter members and wherein all of the retainer members are configured to limit radial expansion of the plurality of filter members.

17. The filter according to claim 16, wherein each retainer member comprises a portion that extends beyond a diameter of the filter basket.

18. The filter according to claim 13, wherein the plurality of filter members have a helical form.

19. The filter according to claim 13, further comprising a band coupled to the extended sections of the plurality of filter members and configured to bind the extended sections together.

* * * * *